United States Patent [19]
Miyoshi et al.

[11] Patent Number: 4,919,922
[45] Date of Patent: Apr. 24, 1990

[54] POLYOLEFIN-TREATED PIGMENT AND COSMETICS CONTAINING THE SAME

[75] Inventors: Ryota Miyoshi, Yono; Isao Imai, Kuki; Tadashi Sugaya, Iwatsuki, all of Japan

[73] Assignee: Miyoshi Kasei Co. Ltd., Urawa, Japan

[21] Appl. No.: 396,822

[22] Filed: Aug. 21, 1989

Related U.S. Application Data

[63] Continuation of Ser. No. 146,670, Jan. 21, 1988, abandoned.

[30] Foreign Application Priority Data

Jan. 21, 1987 [JP] Japan .................................. 62-012044

[51] Int. Cl.$^5$ ...................... A61K 7/021; A61K 31/74; C08K 9/00; C08J 39/00
[52] U.S. Cl. .......................................... 424/63; 424/78; 424/407; 523/205; 524/556; 524/576; 106/502
[58] Field of Search ...................... 424/78, 407, 83, 63; 523/205; 524/556, 576; 106/502

[56] References Cited

U.S. PATENT DOCUMENTS

| | | | |
|---|---|---|---|
| 3,883,458 | 5/1975 | Mueller et al. | 525/285 |
| 4,082,558 | 4/1978 | Nobuo | 524/487 |
| 4,535,049 | 8/1985 | Honda et al. | 430/137 |

FOREIGN PATENT DOCUMENTS 1300223 12/1972 United Kingdom .................. 424/78

*Primary Examiner*—Joseph L. Schofer
*Assistant Examiner*—Carmen B. Pili-Curtis
*Attorney, Agent, or Firm*—Armstrong, Nikaido, Marmelstein, Kubovcik & Murray

[57] ABSTRACT

Pigment with its surface coated with a polyolefin carrying-COOR groups (wherein R is hydrogen atom or a metal atom) is water-repellent and has very high affinity for oily cosmetic components. Cosmetic products containing said surface-treated pigment is excellent in spreadability and feeling.

4 Claims, No Drawings

POLYOLEFIN-TREATED PIGMENT AND COSMETICS CONTAINING THE SAME

This application is a continuation of application Ser. No. 146,670 filed Aug. 21, 1988, now abandoned.

BACKGROUND OF THE INVENTION

1. Field of the Invention

This invention relates to polyolefin-treated pigment and cosmetics containing the same.

2. Description of the Prior Art

Conventional make-up cosmetics, typified by powder foundation, rouge and eyeshadow, contain a metal soap or employ water-repellent pigment with its surface coated with silicone or metal soap so as not to go out of shape due to perspiration, to remain attached to the skin over long periods, and to readily be mixed with oily cosmetic components.

However, addition of a metal soap is not sufficiently effective in imparting high water-repellency and in improving affinity for oily cosmetic components.

Make-up cosmetics employing pigment with its surface treated with a metal soap adhere well to the skin but are still poor in spreadability and feeling.

Many types of cosmetics employing silicone-treated pigment have been used, but these are not satisfactory in adherence to the skin and affinity for oily components although excellent in water-repellency and spreadability.

In order to avoid such disadvantages as mentioned above, many attempts have been made and put to practical use.

For example, cases are known in which, the above-mentioned surface-treating agent is used in combination with other oily substance, such as mineral oils (e.g., liquid paraffin), animal oils (e.g., squalane and lanolin), fatty acids and esters thereof (e.g., myristic and stearic acids), vegetable oils (e.g., olive oil and avocado oil), and paraffin and natural waxes.

In some of these cases, improvement has been achieved to a greater or lesser extent in spreadability and feeling, but the problems are discoloration due to heating in the surface-treatment step and evolution of disagreeable odor caused by deterioration.

SUMMARY OF THE INVENTION

One object of this invention is to provide pigment with high affinity for oily cosmetic components prepared by treating the surface of an hydrophilic, inorganic pigment.

Another object of this invention is to provide cosmetics containing said surface-treated pigment and excellent in spreadability and feeling.

We considered that, if the surface of a hydrophilic, inorganic pigment (including extender pigment) is previously treated with a substance having high affinity for oily cosmetic components (coating or adsorption), the oily components added in the succeeding cosmetics manufacturing step will mix with the pigment more intimately, leading to better spreadability and feeling of the final products. Experiments in search for desirable surface-treating agents under the above assumption have led us to accomplish this invention.

Thus, the pigment of this invention has the surface coated with a polyolefin carrying —COOR groups (in which R is hydrogen atom or a metal atom).

This surface-treating agent has extremely high affinity for oily cosmetic components. Hence, the oily components added in the subsequent cosmetics manufacturing step will form uniform oily film on the treated surface of pigment, thus giving cosmetic products with outstandingly high spreadability. The cosmetic products of this invention also feel smooth and not greasy because the oily components exhibit their effects in small amounts.

DETAILED DESCRIPTION OF THE INVENTION

The carboxyl-containing polyolefins used in this invention are polyethylenes, polypropylenes and polybutenes having a relatively low average molecular weight in the range from about 500 to about 20000. Of these, polyolefins with an average molecular weight less than 5000 are particularly preferable because their film is readily swollen by oily components, thus giving cosmetic products with soft and limber feeling.

Polyethylene is preferable to polybutene in that it gives products which feel smooth and not greasy. However, sticky resins like polybutene are preferred for the manufacture of press cakes which require satisfactory compression molding characteristics.

The carboxyl-containing polyolefins used in this invention may be prepared in two ways: oxidation of a polyolefin, or copolymerization of a monomeric olefin with a bivalent unsaturated organic acid (fumaric or maleic acid is generally used). The preferable acid value of the carboxyl-containing polyolefin is in the range from 5 to 100. If the acid value is less than 5, the resin is difficult to be emulsified in water and hence cannot be adsorbed on pigment in an oriented form. On the other hand, resins with an acid value higher than 100 are not preferable because of the high hydrophilicity.

The carboxyl-containing polyolefins include commercially available oxidized polyethylene, oxidized polypropylene, maleic-acid-modified polyethylene and maleic-acid-modified polypropylene, but are not limited thereto.

Such a carboxyl-containing polyolefin as mentioned above is dissolved in a suitable solvent (e.g., petroleum and aromatic hydrocarbons), the pigment to be surface-treated is added to the resulting solution, and the mixture is thoroughly mixed and dried. Drying methods accompanied by little agglomeration of treated pigment, such as use of a fluidized-bed dryer and of a jet-stream dryer, are preferable.

When a polyolefin carrying carboxyl groups with the hydrogen atoms replaced by metal atoms is to be adsorbed on pigment surface in an oriented form, the pigment is first dispersed in water, a solution of the carboxyl-containing polyolefin (0.5 to 10% based on the weight of pigment) is added to the aqueous dispersion to form an aqueous emulsion or solution of said polyolefin, and then an aqueous solution of a soluble salt of Al, Mg, Ca, Zn, Zr or Ti (0.5 to 5 equivalent proportions based on the carboxyl groups) is added dropwise. The carboxyl-containing polyolefin is thus converted to an insoluble metal salt, which is adsorbed on the surface of pigment in an oriented form. Normally, the surface-treated pigment is collected from the resulting suspension, dehydrated, dried and pulverized before use; but the suspension obtained above may be added, without further treatment, to a liquid cosmetic composition.

As examples of the pigment (including extender pigment) used in this invention, there may be mentioned inorganic pigment, such as titanium dioxide, aluminum oxide, zinc oxide, zirconium oxide, red oxide, yellow oxide, black oxide of iron, Ultramarine blue, Prussian blue, chromium oxide and chromium hydroxide; mica, such as talc, kaolin, muscovite and sericite; extender pigment, such as magnesium carbonate, calcium carbonate, aluminum silicate, magnesium silicate, calcium silicate and clays; mica-titanium; bismuth oxychloride; silica beads; plastic beads, such as nylon, acrylic and polyethylene beads; tar dyes; natural dyes; and other pigment commonly employed in cosmetic and industrial applications.

Typical examples of the soluble salts of Al, Mg, Ca, Zn, Zr and Ti used in this invention include aluminum sulfate, aluminum chloride, aluminum nitrate, potassium aluminum sulfate, magnesium chloride, magnesium sulfate, magneisum nitrate, potassium magnesium sulfate, calcium chloride, calcium nitrate, calcium acetate, zinc chloride, zinc nitrate, zinc sulfate, zinc acetate, zirconium sulfate, zirconium chloride, titanium oxysulfate and titanium tetrachloride.

The carboxyl-containing polyolefin may be solubilized or emulsified in water generally by dissolving it in a petroleum or aromatic solvent and adding to this solution a neutralizer in an amount of 0.5 to 2.0 equivalent proportions based on the carboxyl groups. As the neutralizer, may be used caustic soda, caustic potash, lithium hydroxide, ammonia or an amine either alone or in combination.

The preferable amount of carboxyl-containing polyolefin to be coated on the surface of pigment (including extender pigment) is in the range from 0.5 to 10 weight %. An amount less than 0.5 weight % shows little effect to improve the feeling of final products, while an amount larger than 10 weight % tends to cause agglomeration of the pigment. In combination with the carboxyl-containing polyolefin, may also be used a lipophilic substance, such as silicone, metal soaps, acylamino acids and lecithin, vegetable oil, animal oil, mineral oil or a hydrogenated product thereof, or other additive.

The treated pigment thus obtained can be used in the ordinary cosmetics manufacturing step, thus giving cosmetic products with smooth and agreeable feeling. The pigment surface-treated with a polyolefin carrying carboxyl groups in which the hydrogen atoms have been replaced by metal atoms also show high water-repellency, thus giving excellent make-up cosmetics which remain attached to the skin over long periods. It is preferable that all the pigment used in the cosmetics be treated with a polyolefin as defined above, but pigment otherwise may also be used in combination.

DESCRIPTION OF THE PREFERRED EMBODIMENTS

The following examples will further illustrate the invention but are not intended to limit its scope.

EXAMPLE 1

Twenty grams of maleic-acid-modified polyethylene wax (PO Wax H-10 of Nippon Oil Co., Ltd.; acid value: about 80) was dissolved in 100 g toluene by heating, 500 g mica was added to the solution, and the mixture was treated in a Honschel mixer. After addition of 10 g liquid paraffin, mixing was continued and toluene was removed by evaporation. The surface-treated powder thus obtained showed high water-repellency and had smooth feeling compared with the untreated mica.

EXAMPLE 2

Component 1

Sericite (50 g), talc (8 g), mica (3 g), mica-titanium (3 g), titanium dioxide (19 g), yellow oxide (3 g), red oxide (1 g) and black oxide of iron (0.2 g) were evenly dispersed in 500 ml water.

Separately, 1.5 g of oxidized polyolefin (4202-E of Mitsui Petrochemical Industries, Ltd.; acid value: about 17; average molecular weight: about 2600) was dissolved in a mixture of 5 g xylene and 5 g isopropanol, the solution was neutralized with 1.5 equivalent proportions of aqueous KOH solution, and this neutralized solution was added to the aqueous dispersion prepared above with stirring to effect emulsification. One milliliter of 15% aqueous solution of aluminum sulfate was then added, stirring was continued for ten minutes, and the solid was collected by suction filtration and dried at 105° C. for 16 hours, giving highly water-repellent, surface-treated pigment.

Component 2

A mixture of liquid paraffin (5 g), methylpolysiloxane (3 g), isopropyl myristate (2 g), paraffin wax (1 g), a surface-active agent (1 g), a preservative (0.2 g) and perfume (0.5 g) was heated until a clear solution was obtained.

Component 1 (treated pigment) was pulverized in an atomizer, Component 2 was added, the resulting mixture was treated in a mixer and then in a crusher for 20 minutes, and the powder thus obtained was sifted through a 60-mesh screen and dispensed in containers, giving final products (powder foundation). It is a two-way type foundation with high water-repellency which can be applied by means of dry or water-soaked sponge.

COMPARATIVE EXAMPLE 1

Component 1

Sericite (50 g), talc (8 g), mica (3 g), micatitanium (3 g), titanium dioxide (19 g), yellow oxide (3 g), red oxide (1 g) and black oxide of iron (0.2 g) were mixed well, a solution of 1.75 g methylpolysiloxane in 15 g benzene was added, and the mixture was treated in a home mixer for five minutes. After benzene was removed by air-drying at room temperature, the resulting powder was heat-treated at 120° C. for three hours.

Component 2

Same composition as in Example 2.

Two-way type powder foundation was prepared in the same manner as in Example 2. Table 1 compares the products obtained in Example 2 and Comparative Example 1

TABLE 1

|  | Example 1 | Comparative Example 1 |
|---|---|---|
| Attachment to the skin | ◎ | ▲ |
| Spreadability | ○ | ○ |
| Feeling | ◎ | ▲ |

EXAMPLE 3

Component 1

Sericite (450 g), talc (120 g), mica (200 g), kaolin (100 g), titanium dioxide (90 g), yellow oxide (20 g) and red oxide (20 g) were evenly dispersed in 4 liters of water.

Separately, 10 g of polyethylene wax FB (product of BASF; acid value: about 12; average molecular weight: about 3000) was dissolved in a mixture of 50 g toluene and 50 g isopropanol, the solution was neutralized with 2 equivalent proportions of aqueous NaOH solution, and this neutralized solution was added to the aqueous dispersion prepared above with stirring to effect emulsification. Eight milliliters of 15% aqueous solution of zinc sulfate was then added, stirring was continued for ten minutes, and the resulting mixture was dewatered by means of a centrifugal dryer, giving pigment paste with a water content of about 50%.

Component 2

A mixture of liquid paraffin (3.5 g), squalane (5.0 g), stearyl alcohol (3.0 g), lanolin (1.0 g), a surface-active agent (1.5 g) and a preservative (0.2 g) was heated until a clear solution was obtained.

Component 3

Propylene glycol (5.0 g), deionized water (40.0 g) and perfume (0.8 g) were mixed together.

A mixture of 40 g Component 1 (treated pigment of 50% water content) with Component 2 (hot solution) was thoroughly kneaded and then treated in a homogenizer at 70° C., Component 3 previously heated to 70° C. was slowly added over a period of five minutes, and the resulting mixture was stirred for an additional ten minutes to complete emulsification. After cooling, it was dispensed in containers, giving final products.

The liquid-type foundation thus prepared proved to be an excellent cosmetic product which feels very smooth, adheres well to the skin, and remains attached to the skin for long periods.

As is apparent from the foregoing, the pigment (including extender pigment) of this invention with its surface coated with a polyolefin carrying —COOR groups (in which R is hydrogen atom or a metal salt) is imparted with water-repellency and has high affinity for oily components.

Thus, use of this surface-treated pigment gives cosmetic products of this invention in which the oily components subsequently added form uniform film on the pigment surface.

Because of the high affinity for oily substances, the surface-treated pigment of this invention may also be used in paint, as filler in plastics and for other industrial applications.

What is claimed is:

1. A surface-treated pigment having excellent spreadability and feeling, said pigment consisting essentially of pigment particles, wherein the surfaces of the pigment particles are coated with a coating consisting essentially of a polyolefin which contains —COOR groups, wherein R is a metal atom selected from the group consisting of Al, Mg, Ca, Zn, Zr and Ti, said polyolefin containing —COOR groups having a molecular weight in the range from 500 to 20,000, and an acid value in the range from 5 to 100, the amount of said polyolefin containing —COOR groups being in the range from 0.5 to 10% by weight based on the weight of pigment.

2. A pigment according to claim 1, wherein said polyolefin is adsorbed on the pigment surfaces in an oriented manner so that the metal atom R in said polyolefin is more closely adsorbed to the pigment surface than the remaining portion of said polyolefin.

3. A pigment according to claim 1, wherein said metal atom is selected from the group consisting of Al, Zr and Ti.

4. A pigment according to claim 1, wherein said polyolefin is a member selected from the group consisting of polyethylenes, polypropylenes and polybutenes.

* * * * *